United States Patent [19]

Cherkofsky

[11] 4,267,184

[45] May 12, 1981

[54] ANTIINFLAMMATORY 4,5-DIARYL-2-(SUBSTITUTED-THIO)PYRROLES AND THEIR CORRESPONDING SULFOXIDES AND SULFONES

[75] Inventor: Saul C. Cherkofsky, Wilmington, Del.

[73] Assignee: E. I. Du Pont de Nemours and Company, Wilmington, Del.

[21] Appl. No.: 122,501

[22] Filed: Feb. 19, 1980

Related U.S. Application Data

[63] Continuation-in-part of Ser. No. 10,259, Feb. 8, 1979, abandoned, which is a continuation-in-part of Ser. No. 972,201, Dec. 28, 1978, abandoned, which is a continuation-in-part of Ser. No. 886,337, Mar. 13, 1978, abandoned.

[51] Int. Cl.$^3$ .................. C07D 207/48; C07D 207/36; C07D 401/04; C07D 409/04

[52] U.S. Cl. .................. 424/263; 260/326.35; 260/326.4; 260/326.43; 260/326.5 SM; 260/326.5 S; 260/326.5 SF; 326/326.9; 546/256; 546/280; 546/281; 424/274

[58] Field of Search .................. 260/326.9, 326.5 SM, 260/326.5 S, 326.5 SF, 326.35, 326.4, 326.43; 546/281, 256, 280; 424/263, 274

[56] References Cited

U.S. PATENT DOCUMENTS 3,709,906   1/1973   Yoshida et al. .............. 260/326.5 M

OTHER PUBLICATIONS

Haas et al. Ber. Deut. Chem., vol. 110, pp. 67–77, (1977).

*Primary Examiner*—Alton D. Rollins

[57] ABSTRACT

Antiinflammatory 4,5-diaryl-2-(substituted-thio)pyrroles and their corresponding sulfoxides and sulfones, useful for treating arthritis and related diseases.

72 Claims, No Drawings

ANTIINFLAMMATORY 4,5-DIARYL-2-(SUBSTITUTED-THIO)PYRROLES AND THEIR CORRESPONDING SULFOXIDES AND SULFONES

CROSS REFERENCE TO RELATED APPLICATIONS

This application is a continuation-in-part of my copending application Ser. No. 010,259, filed Feb. 8, 1979, abandoned, which is a continuation-in-part of Ser. No. 972,201, filed Dec. 28, 1978, abandoned, which is a continuation-in-part of Ser. No. 886,337, filed Mar. 13, 1978, abandoned.

BACKGROUND OF THE INVENTION

This invention relates to antiinflammatory pyrroles. J. Szmuszkovicz et al. *J. Med. Chem.*, 9 (4), 527–36 (1966) describe synthesis and biological activity of a clinically tested antiinflammatory agent of the formula

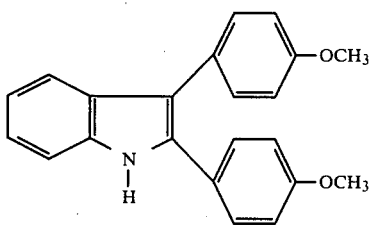

Yoshida et al. U.S. Pat. No. 3,709,906 disclose 2-alkyl-4,5-diphenylpyrrole derivatives which are useful as antiinflammatory agents.

There is a continuing need for safe and effective antiinflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited because of toxicity and adverse side-effects. Many produce gastric irritation and other effects, such as changes in blood cells and central nervous system. Adreno-cortical steroids produce gastric irritation and suppression of normal adrenal function.

In addition to antiinflammatory properties, compounds within the scope of this invention have demonstrated analgesic activity in a test procedure. This additional property is desirable in treatment of arthritis or related diseases; however, the compounds which exhibit this property can be employed solely to alleviate pain.

SUMMARY OF THE INVENTION

This invention relates to compounds of formula I, pharmaceutical compositions containing them and methods of use of these compounds to treat arthritis or alleviate pain in mammals.

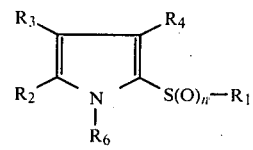

where
$R_1 = C_1$–$C_4$ alkyl, $C_1$–$C_4$ mono- or polyfluoroalkyl or allyl;
$R_2$ and $R_3$, independently, = 2-thienyl, 3-pyridyl 3-pyridyl-N→oxide or

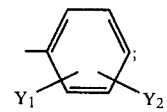

$Y_1 = C_1$–$C_4$ alkyl, $C_1$–$C_4$ alkoxy, F, Cl, Br, H, $(R_5)_2N$ or $R_5S(O)_m$ wherein $R_5$ = methyl or ethyl and $m$ = 0, 1 or 2;
$Y_2 =$ H, F or Cl;
$R_4 =$ H or $C_1$–$C_5$ alkyl;
$R_6 =$ H, $C_1$–$C_4$ alkyl, allyl, —$CH_2CH_2N(R_7)_2$,

2-tetrahydropyranyl, 2-tetrahydrofuranyl,

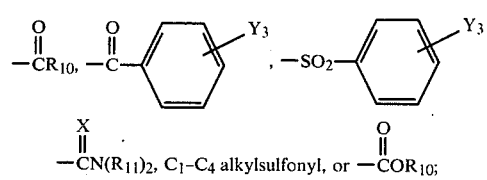

$R_7 =$ H, methyl or ethyl;
$R_8 =$ H or methyl;
$R_9 = C_1$–$C_3$ alkyl, benzyl, —$CH_2CH_2OCH_3$, or

$R_{10} = C_1$–$C_4$ alkyl or benzyl;
$R_{11} =$ methyl or ethyl;
$X =$ O or S;
$Y_3 =$ H, F, Cl, Br, $C_1$–$C_4$ alkyl, $C_1$–$C_4$ alkoxy or nitro;
$n =$ 0, 1 or 2;
provided that when $R_2$ and $R_3$ both =

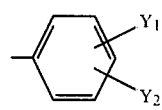

where $Y_1$ and $Y_2$ both = H, $R_1$ is $CF_3$; and further provided that when
$R_1 = CH_3$, $R_2 =$ $R_3 =$

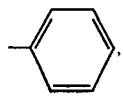

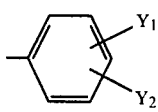

where one of $Y_1$ and $Y_2 = F$ and the other is H, $R_4 = H$ and $R_6 = H$, n cannot be 2;

or its pharmaceutically suitable acid addition salt where at least one of $R_2$ or $R_3 = 3$-pyridyl, $Y_1 = (R_5)_2N$, or $R_6 = -CH_2CH_2N(R_7)_2$.

DETAILED DESCRIPTION OF THE INVENTION

Preferred Compounds

Compounds preferred for their degree of activity, safety and/or ease of synthesis include those where independently:

(a) $R_1 =$ methyl or trifluoromethyl; or
(b) $R_1 =$ methyl and $n = 2$; or
(c) $R_1 =$ trifluoromethyl and $n = 2$; or
(d) $R_2$ and $R_3$, independently, are

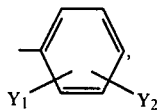

and preferably $Y_1 = F$, Cl, methoxy and more preferably F; $Y_2 = H$; or (e) $R_2 = 3$-pyridyl; or
(f) $R_4 = H$; or
(g) $R_6 = H$; or
(h) $n = 0$ or 2 and more preferably $n = 2$.

Compounds of a preferred scope include those where:
$R_1 =$ methyl or trifluoromethyl;
$R_2$ and $R_3$ are

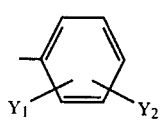

and $Y_1 = F$, Cl or methoxy and more preferably F; $Y_2 = H$;
$R_4 = H$;
$R_6 = H$; and
$n = 0$ or 2 and more preferably $n = 2$.

Examples of compounds preferred for their activity are where
$R_1 = CF_3$;
$R_2$ and $R_3$ both $=$

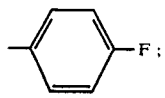

$R_4 = H$;
$R_6 = H$; and
$n = 0, 1$ or 2.

Other examples of preferred compounds are where (A)
$R_1 = CF_3$;
$R_2 = 3$-pyridyl;
$R_3 = C_6H_5$;
$R_4 = H$;
$R_6 = H$; and
$n = 0$.

(B)
$R_1 = CF_3$;
$R_2 =$

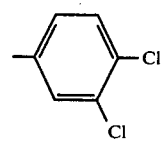

$R_3 = C_6H_5$;
$R_4 = H$;
$R_6 = H$; and
$n = 0$.

(C)
$R_1 = CF_3$
$R_2$ and $R_3$ both $=$

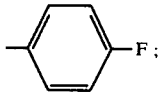

$R_4 = CH_3$;
$R_6 = H$; and
$n = 0$.

(D)
$R_1 = CF_3$;
$R_2 = 3$-pyridyl
$R_3 =$

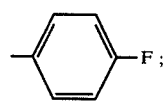

$R_4 = H$;
$R_6 = H$; and
$n = 0$.

Synthesis

The compounds of this invention can be prepared from 2,3-diarylpyrroles. One method of preparation of 2,3-diarylpyrroles involves reaction of substituted α-aminodeoxybenzoins with acetylene diesters, followed by hydrolysis and decarboxylation according to the procedure used by J. Szmuszkovicz et al, *J. Med. Chem.*, 9, 527 (1966) and U.S. Pat. No. 3,462,451 for the synthesis of 2,3-bis(4-methoxyphenyl)pyrrole. (Scheme I).

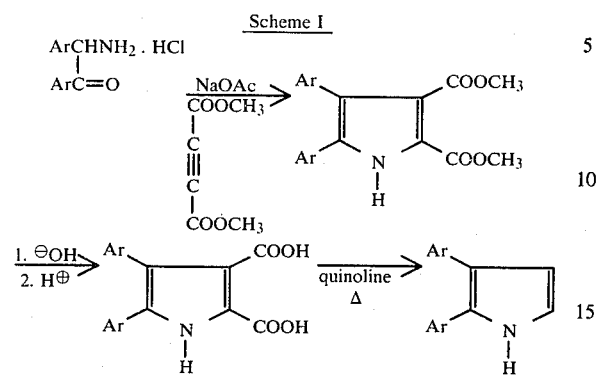

Another method of preparation of 2,3-diarylpyrroles is a modification of the procedure of T. Severin and H. Poehlmann, Chem. Ber., 110, 491 (1977), which describes the preparation of monoaryl pyrroles. By using substituted desoxybenzoins, the desired 2,3-diarylpyrroles result (Scheme II).

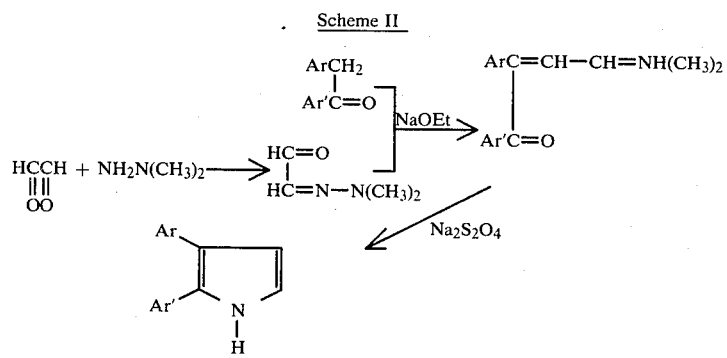

Preparation of 4,5-diaryl-3-alkylpyrroles can be accomplished by several methods. First, 4,5-diarylpyrrole-3-carboxylate esters, prepared, for instance, by the method of A. M. van Leusen et al., Tet. Letters; 5337 (1972) can be reduced to the 4,5-diaryl-3-methylpyrroles by lithium aluminum hydride [following the general procedure of R. L. Hinman and S. Theodoropulos, J. Org. Chem., 28, 3052 (1963)].

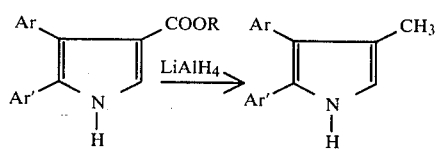

Secondly, 4,5-diaryl-3-propylpyrroles can be prepared by the thio-Claisen rearrangement of 2-allylthiopyrroles, followed by Raney nickel reduction [general procedure of K. Teo et al., Can. J. Chem., 56, 221 (1978)].

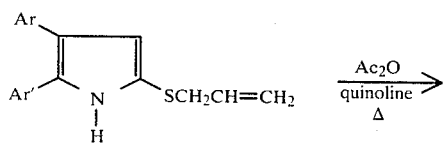

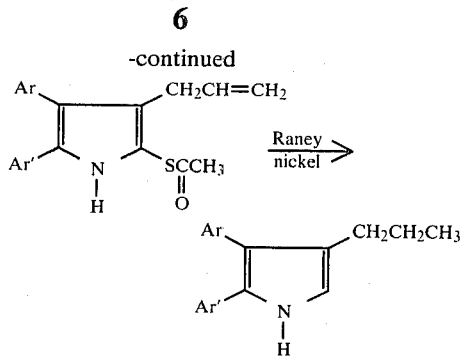

Thirdly, 4,5-diaryl-3-alkylpyrroles can be prepared by the general procedure of N. Engel and, W. Steglich, Angew. Chem. Int. Ed. Engl., 17, 676 (1978), from N-allylcarboxamides.

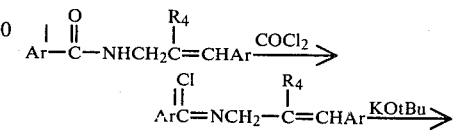

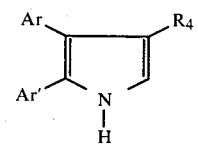

Introduction of an alkylthio functionality is accomplished in several ways. First, trifluoromethanesulfenyl chloride reacts directly and nearly quantitatively with diarylpyrroles to give the 2-trifluoromethylthio substituted compounds.

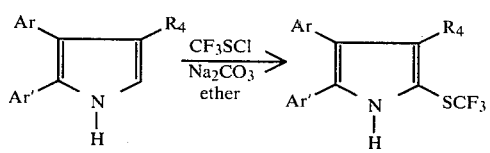

Secondly, other alkylthio pyrroles can also be prepared directly by the reaction of an alkanesulfenyl chloride (such as methanesulfenyl chloride) with a 2,3-diarylpyrrole in an inert organic solvent, such as tetrahydrofuran, diethyl ether, or dioxane, at temperatures from −80° C. to 25° C.

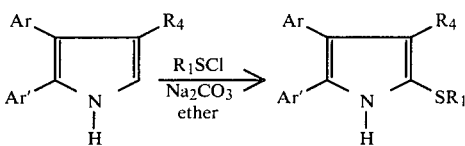

Thirdly, introduction of other alkylthio groups is also accomplished in a two step procedure involving substitution by cupric thiocyanate, thiocyanogen or the like to give the 2-thiocyanate derivative, then hydrolysis in the presence of an alkyl halide, e.g., methyl iodide, or fluorinated olefin, e.g., tetrafluoroethylene.

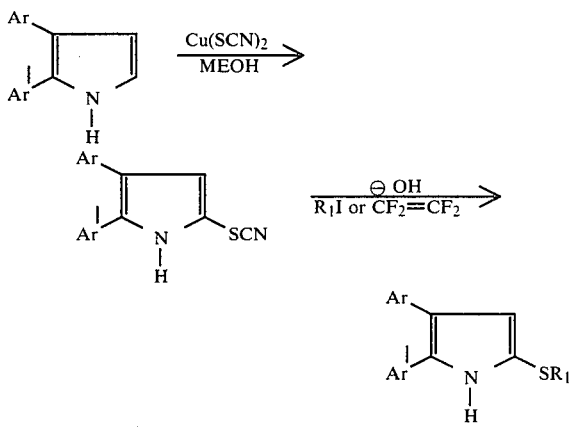

Fourthly, trifluoromethanesulfenyl chloride reacts with 4,5-diarylpyrrole-2-carboxaldehydes and 4,5-diarylpyrrole-2-carboxylic acids to give 4,5-diaryl-2-(trifluoromethylthio)pyrroles directly (with concomitant loss of carbon monoxide and carbon dioxide respectively).

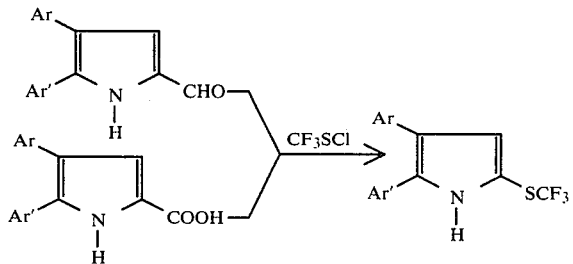

Oxidation of the 2-alkylthio compounds with suitable oxidizing agents, such as m-chloroperoxybenzoic acid (mClPBA) gives the corresponding sulfoxides and sulfones.

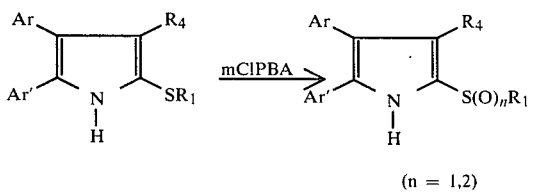

(n = 1,2)

The $R_6$-substituent other than hydrogen of formula I can be introduced by direct alkylation, acylation, or sulfonylation of the compounds of formula I where $R_6$=H. This reaction can be carried out in the absence or presence of a base, such as potassium carbonate, pyridine, triethylamine, potassium t-butoxide, methyl lithium, dimsyl sodium or the like. The reaction can be run neat, using the reagent as solvent, or in the presence of an inert solvent, including but not limited to dimethylformamide, glyme, THF, pyridine and methylene chloride. The temperature of the reaction can be in the range −78° C. to the boiling point of the solvent or reagent, if used in excess as the solvent. Examples of alkylating, acylating and sulfonylating agents that can be employed are allyl halides; alkyl halides such as methyl iodide; dimethylaminoethyl chloride; alkoxymethyl halides, such as benzyloxymethyl chloride; acyloxymethyl halides, such as chloromethylpivalate; dihydropyran; ethyl vinyl ether; 2-chlorotetrahydrofuran; alkyl chloroformates, such as ethyl chloroformate; dialkylcarbamoyl chlorides, such as diethylcarbamoyl chloride; dialkylthiocarbamoyl chlorides such as diethylthiocarbamoyl chloride; alkanoic anhydrides and alkanoyl halides, such as acetic anhydride, aroyl halides, such as benzoyl chloride; alkanesulfonyl halides such as methanesulfonyl chloride; arylsulfonyl halides, such as benzenesulfonyl chloride.

Preparation of pharmaceutically suitable salts of compounds of formula I can be in accordance with well-known techniques of forming salts.

The preparation of these compounds is further illustrated by the following Examples. All parts are by weight and temperatures are in degrees centigrade unless otherwise specified.

PREPARATION 1

2,3-Diphenylpyrrole (Method A)

A. Dimethyl 4,5-diphenylpyrrole-2,3-dicarboxylate

In a 2 l RB 3-neck flask with mechanical stirrer and condenser was placed 76.7 g (0.31 mole) of desyl amine hydrochloride [Pschorr et al, Chem. Ber., 35, 2740 (1902)], 750 ml methanol, 88 g (0.62 mole) dimethyl acetylenedicarboxylate (freshly distilled) and 61 g (0.75 mole) anhydrous sodium acetate. The mixture was heated at reflux for two hours. Then another 44 g (0.31 mole) of dimethyl acetylenedicarboxylate was added and heating continued another two hours. While the reaction mixture was still at reflux, concentrated hydrochloric acid (∼60 ml, to pH∼2) was added dropwise. The mixture was heated at reflux another hour, then poured into 2 l water containing 200 ml 10% sodium bicarbonate solution. With stirring, more sodium bicarbonate was added until the solution was neutral. The gummy solid which precipitated was collected and washed with water. Trituration of this gummy material with ∼500 ml of 50% aqueous ethanol gave a tan powdery solid, which was recrystallized from ∼85% aqueous ethanol to give 65.5 g (63%) of white crystals, m.p. 191°-2° [Lit. m.p. 185°-7°; J. B. Hendrickson et al, J. Am. Chem. Soc., 86, 107 (1964)].

B. 4,5-Diphenylpyrrole-2,3-dicarboxylic Acid

To a mixture of 57.5 g (0.172 mole) of dimethyl 4,5-diphenylpyrrole-2,3-dicarboxylate in 350 ml methanol was added a solution of 71 g (1.78 mole) of sodium hydroxide in 350 ml water. The mixture was heated at reflux for two hours, then cooled in an ice bath. The insoluble white crystals were collected and washed with cold methanol to give the bis sodium salt of the product. The still damp solid was dissolved in 1 l cold water and acidified with conc. hydrochloric acid. The precipitated product was collected by filtration, washed with water containing ∼1% hydrochloric acid, then air dried and finally dried in a vacuum oven at 100° to give 50.0 g (95%) of white solid, m.p. 216°–218° (dec., depends on heating rate).

C. 2,3-Diphenylpyrrole (Method A)

A mixture of 20 g (0.065 mole) of 4,5-diphenylpyrrole-2,3-dicarboxylic acid in 80 ml quinoline was heated at reflux in an oil bath (bath ~230°) until gas evolution stopped (approx. one-half hour). The reaction mixture was cooled and most of the quinoline was removed by distillation (bp 58° @ 0.2 mm). The partially crystalline residue was chromatographed on 300 g Silic AR CC-7, eluting with toluene to give 12 g (85%) of faintly pink 2,3-diphenylpyrrole which could be further purified by recrystallization from ethanol/water or by sublimation (~125° @ 0.2 mm) to give white solid, m.p. 132°–3°.

Anal. Calcd. for $C_{16}H_{13}N$: C, 87.64; H, 5.98; N, 6.39. Found: C, 87.99; H, 5.86; N, 6.50.

PREPARATION 2

2,3-Diphenylpyrrole (Method B)

A. Glyoxal mono(dimethylhydrazone) was prepared by the procedure of T. Severin and H. Poehlmann, *Chem. Ber.*, 110, 491 (1977) to give 36.1 g (80%) of pale yellow liquid, bp 109° (22 mm); lit. bp 90° (16 mm).

B. 4-Dimethylhydrazono-1,2-diphenyl-2-buten-1-one

To a mixture of 19.6 g (0.1 mole) desoxybenzoin and 10 g (0.1 mole) of glyoxal mono(dimethylhydrazone) in 100 ml ethanol was added dropwise a solution of sodium ethoxide prepared by dissolving 2.3 g (0.1 mole) sodium metal in 100 ml ethanol. The mixture was heated at reflux for one-half hour. TLC (90/10, toluene/ethyl acetate) showed a small amount of starting desoxybenzoin, so 2.0 g (0.02 mole) of additional glyoxal mono(dimethylhydrazone) was added. Heating was continued another two hours. TLC at this time showed no starting material, and two clean close yellow product spots (isomers). The mixture was poured into 1 l ice water then extracted with methylene chloride. The organic extracts were dried and concentrated on a rotary evaporator to give 28.7 g (100%) of yellow oil. The NMR showed the presence of two major $N(CH_3)_2$ containing materials (product isomers). The crude oil crystallized from isopropanol to give one pure isomer of product, 13.4 g (48%), pale yellow crystals, m.p. 131°–2°.

Anal. Calcd. for $C_{18}H_{18}N_2O$: C, 77.67; H, 6.52; N, 10.06. Found: C, 77.44; H, 6.46; N, 10.17.

C. 2,3-Diphenylpyrrole (Method B)

A mixture of 3.1 g (0.011 mole) of 4-dimethylhydrazono-1,2-diphenyl-2-buten-1-one, 11.2 g (0.064 mole) sodium hydrosulfite in 75 ml ethanol and 37.5 ml water was heated at reflux for three hours. The mixture was cooled and poured into 300 ml ice water. The white crystalline product was collected, washed with water and air dried to give 1.9 g (79%), m.p. 130°–1°, identical to product obtained via the decarboxylation, Method A.

PREPARATION 3

4,5-Diphenyl-3-methylpyrrole

A. Ethyl 4,5-diphenylpyrrole-3-carboxylate was prepared by a procedure similar to that used by A. M. van Leusen et al., *Tet. Letters*, 5337 (1972) for the preparation of the methyl ester. The ethyl ester was obtained as a white solid, m.p. 207°–208.5° (methyl cyclohexane/toluene).

Anal. Calcd. for $C_{19}H_{17}NO_2$: C, 78.33; H, 5.88; N, 4.81. Found: C, 77.92, 77.90; H, 5.87, 5.88; N, 4.60, 4.62.

B. 4,5-Diphenyl-3-methylpyrrole

To a stirred slurry of 0.76 g (20 m moles) of lithium aluminum hydride in 25 ml THF was added dropwise a solution of 0.58 g (2 m moles) of ethyl 4,5-diphenylpyrrole-3-carboxylate in 5 ml THF. The mixture was heated at reflux overnight. After cooling, 0.8 ml water, 2.4 ml 15% sodium hydroxide solution and 0.8 ml water were added dropwise. The solids were removed by filtration and the filtrate concentrated by rotary evaporation. The crystalline residue was purified by chromatography on 50 g Silic AR CC-7, eluting with hexane/toluene (90/10) to give 0.25 g of product, m.p. 163°–4°.

Anal. Calcd. for $C_{17}H_{15}N$: C, 87.51; H, 6.48; N, 6.00. Found: C, 87.77; H, 6.60; N, 5.89.

PREPARATION 4

4,5-Bis(4-chlorophenyl)-3-propylpyrrole

A. 2-Acetylthio-3-allyl-4,5-bis(4-chlorophenyl)pyrrole

A solution of 3.6 g (0.01 mole) of 2-allylthio-4,5-bis(4-chlorophenyl)pyrrole in 20 ml acetic anhydride was added dropwise to 20 ml quinoline preheated at 170°. The mixture was kept at 170° an additional 45 minutes, then cooled. Most of the acetic acid, acetic anhydride and quinoline were removed by distillation under reduced pressure. The residue was chromatographed on 125 g of Silic AR CC-7, eluting with toluene, to give, after recrystallization from hexane/methyl cyclohexane, 2.7 g of white product, m.p. 131°–2°.

Anal. Calcd. for $C_{21}H_{17}Cl_2NOS$: C, 62.69; H, 4.26; N, 3.48. Found: C, 62.48; H, 4.47; N, 3.57.

B. 4,5-Bis(4-chlorophenyl)-3-propylpyrrole

A mixture of 5 g Raney nickel, 0.8 g (2 m moles) of 2-acetylthio-3-allyl-4,5-bis(4-chlorophenyl)pyrrole and 50 ml acetone was heated at reflux under nitrogen for two hours. The mixture was diluted with ethanol and the catalyst was removed by filtration. The filtrate was concentrated by rotary evaporation. The residue was purified by chromatography on 50 g Silic AR CC-7, eluting with hexane/toluene (90/10), to give 0.15 g of white crystals, m.p. 90°–93°.

Mass spectrum calcd. for $C_{19}H_{17}NCl_2$: 329.0738. Found: 329.0759.

Other 2,3-diarylpyrroles prepared by these procedures are given in Table I.

TABLE I 2,3-Diarylpyrroles

| Preparation | Ar | Ar' | $R_4$ | m.p. |
|---|---|---|---|---|
| 5 | 4-$CH_3OC_6H_4$ | 4-$CH_3OC_6H_4$ | H | oil |
| 6 | 4-$FC_6H_4$ | 4-$FC_6H_4$ | H | 119.5–120.5° |
| 7 | 4-$ClC_6H_4$ | 4-$ClC_6H_4$ | H | 124–7° |
| 8 | 4-$FC_6H_4$ | 4-$C_2H_5OC_6H_4$ | H | 118–118.5° |
| 9 | 4-$ClC_6H_4$ | 4-$FC_6H_4$ | H | 102–4° |
| 10 | 4-$FC_6H_4$ | 4-$ClC_6H_4$ | H | 116–118° |
| 11 | 4-$FC_6H_4$ | 4-$CH_3OC_6H_4$ | H | 117–118° |
| 12 | 4-$ClC_6H_4$ | 4-$CH_3OC_6H_4$ | H | 105–110° |
| 13 | 4-$FC_6H_4$ | $C_6H_5$ | H | 137–8° |
| 14 | 4-$ClC_6H_4$ | $C_6H_5$ | H | 124–6° |
| 15 | 4-$CH_3C_6H_4$ | 4-$CH_3C_6H_4$ | H | 128–9° |
| 16 | 3-$FC_6H_4$ | 3-$FC_6H_4$ | H | 90–90.5° |
| 17 | $C_6H_5$ | 3,4-di$ClC_6H_3$ | H | 112–113° |
| 18 | 2-$FC_6H_4$ | 2-$FC_6H_4$ | H | 131–132.5° |
| 19 | $C_6H_5$ | 3-pyridyl | H | 190–192° |
| 20 | 4-$CH_3OC_6H_4$ | 2-thienyl | H | 65–66.5° |

TABLE I-continued 2,3-Diarylpyrroles

Ar, Ar' at 2,3 positions; R4 at position 4; N-H

| Preparation | Ar | Ar' | R4 | m.p. |
|---|---|---|---|---|
| 21 | $C_6H_5$ | 4-$CH_3OC_6H_4$ | H | 77–77.5° |
| 22 | 4-$FC_6H_4$ | 4-$BrC_6H_4$ | H | 129–130° |
| 23 | 4-$FC_6H_4$ | 4-$(CH_3)_2NC_6H_4$ | H | 200–201° |
| 24 | $C_6H_5$ | 4-$FC_6H_4$ | H | 105.5–106.5° |
| 25 | $C_6H_5$ | 4-$ClC_6H_4$ | H | 100–101° |
| 26 | 3-$ClC_6H_4$ | 3-$ClC_6H_4$ | H | oil |
| 27 | 4-$FC_6H_4$ | 4-$CH_3SC_6H_4$ | H | 164–165° |
| 28 | 4-$FC_6H_4$ | 2-thienyl | H | 97–99° |
| 29 | 4-$FC_6H_4$ | 3-pyridyl | H | 173–174° |
| 30 | 4-$FC_6H_4$ | 4-$CH_3SO_2C_6H_4$ | H | 268–270° |
| 31 | 4-$ClC_6H_4$ | 4-$ClC_6H_4$ | $CH_3$ | 132–142° |
| 32 | 4-$FC_6H_4$ | 4-$FC_6H_4$ | $CH_3$ | 126–127° |
| 33 | 4-$CH_3OC_6H_4$ | 4-$CH_3OC_6H_4$ | $CH_3$ | oil |
| 34 | 4-$FC_6H_4$ | 4-$FC_6H_4$ | $CH_3CH_2CH_2$ | 113–115° |

EXAMPLE 1

4,5-Diphenyl-2-(trifluoromethylthio)pyrrole

In glassware flamed out, under nitrogen, and fitted with a dry ice condenser, were placed 11 g (0.05 mole) 2,3-diphenylpyrrole, 6.4 g (0.06 mole) anhydrous sodium carbonate and 200 ml ether. The mixture was chilled to −30° and 7.6 g (0.055 mole) trifluoromethanesulfenyl chloride was added as a gas from a tared trap. The reaction was stirred at −30° one-half hour, then allowed to warm to room temperature for two hours. The inorganic salts were removed by filtration and the ether filtrate was concentrated. The residue was chromatographed on 300 g Silic AR CC-7 eluting with hexane containing 5–10% toluene. The product was obtained as a white solid, 15.4 g (96%), m.p. 58°–9°.

Anal. Calcd. for $C_{17}H_{12}F_3NS$: C, 63.94; H, 3.79; N, 4.39. Found: C, 63.66; H, 3.87; N, 4.34.

EXAMPLE 2

4,5-Bis(4-methoxyphenyl)-2-(trifluoromethylthio)pyrrole

Method A

Following the procedure of Example 1, reaction of 2,3-bis(4-methoxyphenyl)pyrrole with trifluoromethanesulfenyl chloride gave 4,5-bis(4-methoxyphenyl)-2-(trifluoromethylthio)pyrrole as a white solid, m.p. 114°–115°.

Anal. Calcd. for $C_{19}H_{16}F_3NO_2S$: C, 60.14; H, 4.25; N, 3.69. Found: C, 60.24, 60.32; H, 4.29, 4.20; N. 3.67, 3.71.

Method B (a) 4,5-Bis(4-methoxyphenyl)pyrrole-2-carboxaldehyde

To 25 ml DMF at 0° was added dropwise with stirring 30 g of phosphorus oxychloride. The mixture was stirred for 15 minutes at room temperature, then a solution of 5.6 g (0.02 mole) of 2,3-bis(4-methoxyphenyl)pyrrole in 40 ml DMF was added dropwise with cooling in an ice bath. The mixture was then heated at 70°–80° for one hour, then cooled. Aqueous sodium hydroxide (50%) was added until the mixture was basic. The reaction mixture was then heated again at 70° for 15 minutes. The cooled reaction mixture was poured into ice water. The precipitated material was collected and purified by chromatography on 600 g Silic AR CC-7 (eluting with toluene containing 1–2% ethyl acetate) to give 3.4 g (55%) of product, m.p. 165°–6° (methylcyclohexane/toluene).

Anal. Calcd. for $C_{19}H_{17}NO_3$: C, 74.25; H, 5.58; N, 4.56. Found: C, 74.46; H, 5.43; N, 4.44.

(b) 4,5-Bis(4-methoxyphenyl)-2-(trifluoromethylthio)pyrrole

To a stirred mixture of 1.5 g (5 m mole) of 4,5-bis(4-methoxyphenyl)pyrrole-2-carboxaldehyde and 1.3 g sodium carbonate in 10 ml ether/10 ml THF at −78° was added 0.8 g of trifluoromethanesulfenyl chloride. The mixture was allowed to warm to room temperature with a dry-ice condenser attached to keep the trifluoromethanesulfenyl chloride from escaping. Excess trifluoromethanesulfenyl chloride was added and the mixture was stirred overnight at room temperature. The mixture was filtered and the filtrate concentrated by rotary evaporation. The residue was purified by chromatography on 300 g Silic AR CC-7, eluting with toluene, to give 0.75 g (39%) of product, identical to that obtained by Method A.

Method C (a) 4,5-Bis(4-methoxyphenyl)-2-(trifluoroacetyl)pyrrole

To a stirred solution of 2.5 g trifluoroacetic anhydride in 30 ml ether at 0° was added dropwise a solution of 2.8 g (0.01 mole) of 2,3-bis(4-methoxyphenyl)pyrrole and 1.5 g of dimethyl aniline in 20 ml ether. The mixture was stirred one hour at 0°, then diluted with more ether and washed with water, 1 N hydrochloric acid, then water again. The organic layer was dried and concentrated. The residue was purified by chromatography in Silic AR CC-7 (300 g, eluted by toluene), followed by recrystallization from methylcyclohexane to give 2.2 g (59%) of pale yellow crystals, m.p. 185°–186.5°.

Anal. Calcd. for $C_{20}H_{16}F_3NO_3$: C, 64.00; H, 4.30; N, 3.73. Found: C, 64.35, 64.03; H, 4.41, 4.22; N, 3.61, 3.70.

(b) 4,5-Bis(4-methoxyphenyl)pyrrole-2-carboxylic acid

To a refluxing solution of 1.9 g (5 m moles) of 4,5-bis(4-methoxyphenyl)-2-(trifluoroacetyl)pyrrole in 20 ml ethanol was added a solution of 2 g sodium hydroxide in 20 ml water. The mixture was heated at reflux 3½ hours then cooled and diluted with water. The aqueous solution was extracted with methylene chloride. The aqueous layer gave only 0.1 g of acid product upon acidification with hydrochloric acid. The methylene chloride solution of the sodium salt of the acid was acidified by shaking with 1 N hydrochloric acid. The methylene chloride layer was then dried and concentrated to give another 1.1 g of acid product. The combined product was recrystallized from ethanol/water to give 1.2 g (75%) of white product, m.p. 204°–5°.

Anal. Calcd. for $C_{19}H_{17}NO_4$: C, 70.58; H, 5.30; N, 4.33. Found: C, 70.38; H, 5.35; N, 4.44.

(c) 4,5-Bis(4-methoxyphenyl)-2-(trifluoromethylthio)pyrrole

To a solution of 0.3 g (1 m mole) of 4,5-bis(4-methoxyphenyl)pyrrole-2-carboxylic acid in 5 ml ether/5 ml THF at −78° was added as a gas 0.3 g of trifluoromethanesulfenyl chloride. After 15 minutes, TLC showed no evidence of reaction, so a large excess of trifluoromethanesulfenyl chloride was added and the mixture was allowed to warm slowly to room temperature overnight, with a dry ice condenser attached for the first few hours. The reaction mixture was concentrated under reduced pressure and the residue was purified by chromatography on 100 g Silic AR CC-7 to give after recrystallization from hexane 0.15 g (40%) of 4,5-bis(4-methoxyphenyl)-2-(trifluoromethylthio)pyrrole, identical to material obtained by Method A.

Other 4,5-diaryl-2-(trifluoromethylthio)pyrroles prepared by the procedures of Examples 1 and 2A are given in Table II.

TABLE II 4,5-Diaryl-2-(trifluoromethylthio)pyrroles

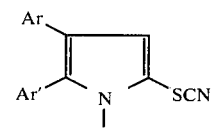

| Example | Ar | Ar' | $R_4$ | m.p. |
|---|---|---|---|---|
| 3 | 4-$FC_6H_4$ | 4-$FC_6H_4$ | H | 106-107.5° |
| 4 | 4-$ClC_6H_4$ | 4-$ClC_6H_4$ | H | 95-96.5° |
| 5 | 4-$FC_6H_4$ | 4-$C_2H_5OC_6H_4$ | H | 83-84° |
| 6 | 4-$ClC_6H_4$ | 4-$FC_6H_4$ | H | 103-4° |
| 7 | 4-$FC_6H_4$ | 4-$ClC_6H_4$ | H | 90-1° |
| 8 | 4-$FC_6H_4$ | 4-$CH_3OC_6H_4$ | H | 122-3° |
| 9 | 4-$ClC_6H_4$ | 4-$CH_3OC_6H_4$ | H | 115-116.5° |
| 10 | 4-$FC_6H_4$ | $C_6H_5$ | H | 78-9° |
| 11 | 4-$ClC_6H_4$ | $C_6H_5$ | H | 98-9° |
| 12 | 4-$CH_3C_6H_4$ | 4-$CH_3C_6H_4$ | H | 79-80° |
| 13 | 3-$FC_6H_4$ | 3-$FC_6H_4$ | H | 74-5° |
| 14 | 4-$ClC_6H_4$ | 4-$ClC_6H_4$ | $CH_3CH_2CH_2$ | 99-100° |
| 15 | $C_6H_5$ | $C_6H_5$ | $CH_3$ | 79-81° |
| 16 | $C_6H_5$ | 3,4-di$ClC_6H_3$ | H | 82-82.5° |
| 17 | $C_6H_5$ | 3-pyridyl | H | 196-197° |
| 18 | 4-$CH_3OC_6H_4$ | 2-thienyl | H | 73-74° |
| 19 | 2-$FC_6H_4$ | 2-$FC_6H_4$ | H | 31-32° |
| 20 | $C_6H_5$ | 4-$CH_3OC_6H_4$ | H | 107-108° |
| 21 | 4-$FC_6H_4$ | 4-$BrC_6H_4$ | H | 92.5-93° |
| 22 | 4-$FC_6H_4$ | 4-$(CH_3)_2NC_6H_4$ | H | 158-159.5° |
| 23 | $C_6H_5$ | 4-$FC_6H_4$ | H | 88-88.5° |
| 24 | $C_6H_5$ | 4-$ClC_6H_4$ | H | 107-108° |
| 25 | 3-$ClC_6H_4$ | 3-$ClC_6H_4$ | H | oil |
| 26 | 4-$FC_6H_4$ | 4-$CH_3SC_6H_4$ | H | 106-107° |
| 27 | 4-$FC_6H_4$ | 2-thienyl | H | 65-66° |
| 28 | 4-$FC_6H_4$ | 3-pyridyl | H | 190-191° |
| 29 | 4-$FC_6H_4$ | 4-$CH_3SO_2C_6H_4$ | H | 203-204° |
| 30 | 4-$ClC_6H_4$ | 4-$ClC_6H_4$ | $CH_3$ | 87-90° |
| 31 | 4-$FC_6H_4$ | 4-$FC_6H_4$ | $CH_3$ | 125-125.5° |
| 32 | 4-$CH_3OC_6H_4$ | 4-$CH_3OC_6H_4$ | $CH_3$ | 132-133° |
| 33 | 4-$FC_6H_4$ | 4-$FC_6H_4$ | $CH_3CH_2CH_2$ | 96.5-97° |

PREPARATION 35

4,5-Diphenyl-2-(thiocyanato)pyrrole

To a mixture of 11 g (0.05 mole) of 2,3-diphenylpyrrole in 150 ml methanol at room temperature was added in portions 18 g (~0.1 mole) cupric thiocyanate. After stirring at room temperature for three hours, TLC indicated approximately 50% starting material was left (no change from two hours), so another 18 g (0.1 mole) cupric thiocyanate was added. After another hour, TLC indicated no starting material. The inorganic material was removed by filtration and the methanol filtrate was concentrated. This residue was taken up in methylene chloride, washed with water, then dried and concentrated. The residue was chromatographed on 300 g Silic AR CC-7, eluting with toluene to give 11.3 g (82%), m.p. 139°-140° (methylcyclohexane).

Anal. Calcd. for $C_{17}H_{12}N_2S$: C, 73.89; H, 4.38; N, 10.14. Found: C, 73.90; H, 4.49; N, 10.31.

Other 4,5-diaryl-2-(thiocyanato)pyrroles prepared in this manner are given in Table III.

TABLE III 4,5-Diaryl-2-(thiocyanato)pyrroles

| Preparation | Ar | Ar' | m.p. |
|---|---|---|---|
| 36 | 4-$CH_3OC_6H_4$ | 4-$CH_3OC_6H_4$ | oil |
| 37 | 4-$FC_6H_4$ | 4-$C_2H_5OC_6H_4$ | 129-131° |
| 38 | 4-$ClC_6H_4$ | 4-$ClC_6H_4$ | 168-9° |
| 39 | 4-$FC_6H_4$ | 4-$FC_6H_4$ | 164-165.5° |
| 40 | 4-$ClC_6H_4$ | 4-$FC_6H_4$ | 150-1° |
| 41 | 4-$FC_6H_4$ | 4-$ClC_6H_4$ | 174-5° |
| 42 | 4-$FC_6H_4$ | 4-$CH_3OC_6H_4$ | 148-9° |
| 43 | 4-$ClC_6H_4$ | 4-$CH_3OC_6H_4$ | 173-4° |
| 44 | 4-$FC_6H_4$ | $C_6H_5$ | 175-6° |
| 45 | 4-$ClC_6H_4$ | $C_6H_5$ | 162-162.5° |
| 46 | 4-$CH_3C_6H_4$ | 4-$CH_3C_6H_4$ | 161-2° |

EXAMPLE 34

4,5-Diphenyl-2-(methylthio)pyrrole

To a mixture of 1.4 g (0.005 mile) 4,5-diphenyl-2-thiocyanatopyrrole, 0.85 g (0.006 mole) methyl iodide in 10 ml methanol was added dropwise at 0° a solution of 0.8 g (~0.012 mole, 85%) potassium hydroxide in 5 ml water+5 ml methanol. The mixture was allowed to warm to room temperature, then was poured into 100 ml ice water and neutralized with hydrochloric acid. The aqueous mixture was extracted with methylene chloride, and the extracts dried and concentrated. The residue was chromatographed on 50 g Silic AR CC-7, eluting with toluene to give 1.2 g (90%) yellow oil.

EXAMPLE 35

4,5-Bis(4-fluorophenyl)-2-(1,1,2,2-tetrafluoroethylthio)-pyrrole

A mixture of 3.1 g (0.01 mole) of 4,5-bis(4-fluorophenyl)-2-(thiocyanato)pyrrole, 10 ml water and 100 ml methanol was placed in a pressure vessel and frozen in dry ice. Then 2.0 g of potassium hydroxide was added. The pressure vessel was evacuated and purged with nitrogen. Then 2.5 g of tetrafluoroethylene was added and the pressure vessel sealed. The mixture was allowed to warm to room temperature and was shaken overnight. The pressure vessel was vented and the contents rinsed out with methanol. The mixture was diluted with water and saturated sodium chloride solution, then extracted with methylene chloride. The organic layers are combined, dried and concentrated by rotary evaporation. The residue was chromatographed on 300 g Silic AR CC-7 eluting with mixtures of hexane and toluene to give, after recrystallization from hexane or ethanol/water 1.8 g of product, m.p. 70.5°-71°.

Anal. Calcd. for $C_{18}H_{11}F_6NS$: C, 55.82; H, 2.86; N, 3.62. Found: C, 55.78; H, 3.08; N, 3.48.

Other 4,5-diaryl-2-(alkylthio)pyrroles prepared in this manner are given in Table IV.

TABLE IV

4,5-Diaryl-2-(alkylthio)pyrroles $$\text{Ar} \underset{\underset{H}{N}}{\overset{Ar'}{\diagdown}} SR_1$$

| Example | Ar | Ar' | $R_1$ | m.p. |
|---|---|---|---|---|
| 36 | 4-$CH_3OC_6H_4$ | 4-$CH_3OC_6H_4$ | $CH_3$ | 164–5° |
| 37 | 4-$CH_3OC_6H_4$ | 4-$CH_3OC_6H_4$ | $CH_3CH_2$ | 82–3° |
| 38 | 4-$ClC_6H_4$ | 4-$ClC_6H_4$ | $CH_3$ | 139–141° |
| 39 | 4-$FC_6H_4$ | 4-$C_2H_5OC_6H_4$ | $CH_3$ | 119.5–120.5° |
| 40 | 4-$ClC_6H_4$ | 4-$ClC_6H_4$ | $CHF_2CF_2$ | oil |
| 41 | 4-$FC_6H_4$ | 4-$FC_6H_4$ | $CH_3$ | 88–88.5° |
| 42 | 4-$ClC_6H_4$ | 4-$ClC_6H_4$ | $CH_3CH_2$ | oil |
| 43 | 4-$ClC_6H_4$ | 4-$FC_6H_4$ | $CH_3$ | 112–112.5° |
| 44 | 4-$FC_6H_4$ | 4-$ClC_6H_4$ | $CH_3$ | 102–102.5° |
| 45 | 4-$FC_6H_4$ | 4-$CH_3OC_6H_4$ | $CH_3$ | 103–5° |
| 46 | 4-$ClC_6H_4$ | 4-$CH_3OC_6H_4$ | $CH_3$ | 149–151° |
| 47 | 4-$FC_6H_4$ | $C_6H_5$ | $CH_3$ | 97–8° |
| 48 | 4-$ClC_6H_4$ | $C_6H_5$ | $CH_3$ | 124–124.5° |
| 49 | 4-$CH_3C_6H_4$ | 4-$CH_3C_6H_4$ | $CH_3$ | 117–118° |
| 50 | 4-$ClC_6H_4$ | 4-$ClC_6H_4$ | $CH_2{=}CHCH_2$ | oil |

EXAMPLES 51, 52

4,5-Diphenyl-2-(trifluoromethylsulfonyl and sulfinyl)pyrrole

To a solution of 9.6 g (0.03 mole) 4,5-diphenyl-2-(trifluoromethylthio)pyrrole in 100 ml methylene chloride at room temperature was added dropwise a solution of 12 g (~0.06 mole, ~85%) m-chloroperoxybenzoic acid in 150 ml methylene chloride. After two hours, TLC (toluene/ethyl acetate, 90/10) showed a trace of sulfide and major amounts of sulfoxide and sulfone. Since a potassium iodide-starch test was negative, an additional 1 g (~0.005 mole) of peracid was added and stirring continued for another two hours (KI-starch test negative, TLC no sulfide left). The mixture was washed twice with 10% sodium bicarbonate, once with water, then dried and concentrated. The residue was chromatographed on ~1 kg Silic AR CC-7. Eluted with toluene was the sulfone, 2.2 g (22%), m.p. 159°–160° (methylcyclohexane), example 51.

Anal. Calcd. for $C_{17}H_{12}F_3NO_2S$: C, 58.12; H, 3.44; N, 3.99. Found: C, 58.25; H, 3.60; N, 4.39.

Eluted with toluene/ethyl acetate (95/5) was the sulfoxide, 0.9 g (9%), m.p. 125°–6° (ethanol/water), example 52.

Anal. Calcd. for $C_{17}H_{12}F_3NOS$: C, 60.89; H, 3.61; N, 4.18. Found: C, 60.99, 61.37; H, 3.45, 4.12; N, 3.94, 4.00.

Other 4,5-diaryl-2-(alkylsulfinyl and sulfonyl)pyrroles prepared in this manner are given in Table V.

TABLE V

4,5-Diaryl-2-(alkylsulfonyl or sulfinyl)pyrroles $$\text{Ar} \underset{\underset{H}{N}}{\overset{Ar'}{\diagdown}} S(O)_nR_1$$

| Example | Ar | Ar' | $R_1$ | n | m.p. |
|---|---|---|---|---|---|
| 53 | 4-$CH_3OC_6H_4$ | 4-$CH_3OC_6H_4$ | $CF_3$ | 2 | 203–204.5° |
| 54 | 4-$CH_3OC_6H_4$ | 4-$CH_3OC_6H_4$ | $CH_3$ | 2 | 142–142.5° |
| 55 | 4-$CH_3OC_6H_4$ | 4-$CH_3OC_6H_4$ | $CH_3CH_2$ | 2 | 136–136.5° |
| 56 | 4-$FC_6H_4$ | 4-$FC_6H_4$ | $CF_3$ | 2 | 154–5° |
| 57 | 4-$FC_6H_4$ | 4-$FC_6H_4$ | $CF_3$ | 1 | 128–9° |
| 58 | 4-$ClC_6H_4$ | 4-$ClC_6H_4$ | $CF_3$ | 2 | 133–5° |
| 59 | 4-$ClC_6H_4$ | 4-$ClC_6H_4$ | $CF_3$ | 1 | 176–176.5° |
| 60 | 4-$FC_6H_4$ | 4-$C_2H_5OC_6H_4$ | $CF_3$ | 2 | 131–2° |
| 61 | 4-$FC_6H_4$ | 4-$C_2H_5OC_6H_4$ | $CF_3$ | 1 | 166–9° |
| 62 | 4-$ClC_6H_4$ | 4-$ClC_6H_4$ | $CH_3$ | 2 | 186–8° |
| 63 | 4-$FC_6H_4$ | 4-$C_2H_5OC_6H_4$ | $CH_3$ | 2 | 149–150° |
| 64 | 4-$FC_6H_4$ | 4-$FC_6H_4$ | $CH_3$ | 2 | 185–6° |
| 65 | 4-$ClC_6H_4$ | 4-$ClC_6H_4$ | $CH_3CH_2$ | 2 | 185–185.5° |
| 66 | 4-$ClC_6H_4$ | 4-$FC_6H_4$ | $CH_3$ | 2 | 212–212.5° |
| 67 | 4-$FC_6H_4$ | 4-$ClC_6H_4$ | $CH_3$ | 2 | 188–9° |
| 68 | 4-$FC_6H_4$ | 4-$CH_3OC_6H_4$ | $CH_3$ | 2 | 182–3° |
| 69 | 4-$ClC_6H_4$ | 4-$CH_3OC_6H_4$ | $CH_3$ | 2 | 211–212° |
| 71 | 4-$ClC_6H_4$ | $C_6H_5$ | $CH_3$ | 2 | 198–9° |
| 72 | 4-$CH_3C_6H_4$ | 4-$CH_3C_6H_4$ | $CH_3$ | 2 | 212–213° |

Table VI illustrates other compounds that can be prepared by the procedures previously described.

TABLE VI $$\text{R}_3 \underset{\underset{H}{N}}{\overset{R_4}{\diagdown}} S(O)_nR_1 \quad R_2$$

| $R_1$ | $R_2$ | $R_3$ | $R_4$ | n |
|---|---|---|---|---|
| —$CH_2CH{=}CH_2$ | 4-$FC_6H_4$ | 4-$FC_6H_4$ | H | 0 |
| —$CH_2CH_2CH_2CH_3$ | 4-$CH_3OC_6H_4$ | 4-$CH_3OC_6H_4$ | H | 2 |
| —$CHF_2$ | 4-$FC_6H_4$ | 4-$FC_6H_4$ | H | 0 |
| —$CF_2CF_3$ | 4-$FC_6H_4$ | 4-$FC_6H_4$ | H | 0 |
| —$CF_3$ | 4-$ClC_6H_4$ | 4-$FC_6H_4$ | H | 2 |
| —$CH_3$ | 4-$FC_6H_4$ | 4-$CH_3OC_6H_4$ | H | 2 |
| —$CF_3$ | 4-$ClC_6H_4$ | 4-$CH_3OC_6H_4$ | H | 0 |
| —$CF_3$ | $C_6H_5$ | 4-$CH_3OC_6H_4$ | H | 0 |
| —$CF_3$ | $C_6H_5$ | 3,4-di$ClC_6H_3$ | H | 2 |
| —$CF_3$ | 4-$FC_6H_4$ | 4-$(CH_3)_2NC_6H_4$ | H | 0 |
| —$CF_3$ | 4-$FC_6H_4$ | 4-$BrC_6H_4$ | H | 0 |
| —$CF_3$ | 4-$FC_6H_4$ | 4-$CH_3CH_2CH_2CH_2C_6H_4$ | H | 0 |
| —$CF_3$ | 4-$FC_6H_4$ | 4-$CH_3CH_2CH_2OC_6H_4$ | H | 0 |
| —$CF_3$ | 4-$FC_6H_4$ | 4-$(C_2H_5)_2NC_6H_4$ | H | 0 |
| —$CH_2CH_2CH_2F$ | 4-$FC_6H_4$ | 4-$FC_6H_4$ | H | 0 |

EXAMPLE 73

1-Acetyl-4,5-bis(4-fluorophenyl)-2-(trifluoromethylthio)pyrrole

A mixture of 1.8 g. of 4,5-bis(4-fluorophenyl)-2-(trifluoromethylthio)pyrrole and 25 ml. of acetic anhydride was heated at reflux with stirring under nitrogen for 2 days and then concentrated under vacuum. The residue was purified by chromatography on Silic AR CC-7 (eluting with hexane and then hexane/toluene) to give 400 mg. of a colorless solid product. Recrystallization from ethanol/H₂O gave an analytical sample, m.p. 75°–76° C.

Anal. Calcd. for $C_{19}H_{12}F_5NOS$: C, 57.43; H. 3.04; N, 3.52; Found: C, 57.05; H, 3.15; N, 3.51.

EXAMPL 74

1-Methyl-4,5-bis(4-fluorophenyl)-2-(trifluoromethylthio)pyrrole

A sodium hydride dispersion (0.45 g.; 9 mmoles) was reacted with 30 ml. of DMSO under nitrogen with stirring. After gas evolution had ceased, a solution of 2.13 g. (6 mmoles) of 4,5-bis(4-fluorophenyl)-2-(trifluoromethylthio)pyrrole in 6 ml. of DMSO was added dropwise at room temperature. After stirring at room temperature for 15 minutes, 2.1 g. (15 mmoles) of methyl iodide was added and the reaction mixture was stirred for 30 minutes. The reaction mixture was then poured into water and the product extracted into ether. The combined ether extracts were washed 3 times with water and, after drying, evaporated to afford 2.3 g of crystals.

The crystals above were combined with 700 mg. of product from a previous run and purified by chromatography on Silic AR CC-7 (eluting with hexane) to give 2.4 g. of product, m.p. 76°–77° C. (ethanol/water).

Anal. Calcd. for $C_{18}H_{12}F_2NS$: C, 58.53; H, 3.27; N, 3.79; Found: C, 58.76; H, 3.48; N, 3.77.

EXAMPLE 75

1-Ethoxycarbonyl-4,5-bis(4-fluorophenyl)-2-(trifluoromethylthio)pyrrole

A mixture of 700 mg. (2 mmoles) of 4,5-bis(4-fluorophenyl)-2-(trifluoromethylthio)pyrrole and 330 mg. (3 mmoles) of potassium tert-butoxide in 20 ml. of toluene was heated to reflux with stirring and then cooled to room temperature under nitrogen. A solution of 700 mg. (6 mmoles) of ethyl chloroformate in 15 ml. of toluene was then added dropwise and the reaction mixture stirred at room temperature for several hours. The mixture was poured onto an aqueous sodium bicarbonate solution and the product extracted into methylene chloride. The combined organic layers were dried and concentrated to give 800 mg. of a viscous oil. The oil was purified by chromatography on Silic AR CC-7 (eluted by hexane and then by mixtures of hexane/toluene), followed by recrystallization from ethanol/water to give 400 mg. of product as colorless crystals, m.p. 54°–54.5° C.

Anal. Calcd. for $C_{20}H_{14}F_5NO_2S$: C, 56.21; H, 3.30; N, 3.28; Found: C, 56.46; H, 3.43; N, 3.16.

EXAMPLE 76

1-Benzoyl-4,5-bis(4-fluorophenyl)-2-(trifluoromethylthio)pyrrole

A mixture of 2.1 g. (6 mmoles) of 4,5-bis-(4-fluorophenyl)-2-(trifluoromethylthio)pyrrole and 1.3 g. (12 mmoles) of potassium tert-butoxide in 60 ml. of toluene was heated to reflux with stirring and then cooled to room temperature under nitrogen. A solution of 1.7 g. of benzoyl chloride in 15 ml. of toluene was then added and the reaction mixture stirred overnight at room temperature. The mixture was diluted with methylene chloride, which was washed with 10% aqueous sodium bicarbonate solution, dried and evaporated. The residue was purified by chromatography on Fisher 100–200 mesh silica gel (eluted by hexane and then by mixtures of hexane/toluene), followed by recrystallization from ethanol/water to afford 1.8 g. of colorless crystals, m.p. 105.5°–106° C.

Anal. Calcd. for $C_{24}H_{14}F_5NOS$: C, 62.74; H, 3.07; N, 3.05; Found: C, 62.83; H, 3.22; N, 2.90.

EXAMPLE 77

1-Benzenesulfonyl-4,5-bis(4-fluorophenyl)-2-trifluoromethylthio)pyrrole

Using the procedure described in Example 75, 700 mg. (2 mmoles) of 4,5-bis(4-fluorophenyl)-2-(trifluoromethylthio)pyrrole was reacted with 530 mg. (3 mmoles) of benzenesulfonyl chloride. The crude reaction product was purified by chromatography on Fisher 100–200 mesh silica gel (eluted by hexane and then by mixtures of hexane/toluene), followed by recrystallization from hexane to give 250 mg. of colorless crystals, m.p. 133°–133.5° C.

Anal. Calcd. for $C_{23}H_{14}F_5NO_2S_2$: C, 55.75; H, 2.85; N, 2.83; Found: C, 55.46; H, 2.88; N, 2.98.

Table VIA illustrates other compounds that can be prepared by the procedures previously described.

TABLE VIA

| $R_1$ | $R_2$ | $R_3$ | $R_4$ | $R_6$ | n |
|---|---|---|---|---|---|
| $CH_2CH=CH_2$ | $4-FCH_4$ | $4-FC_6H_4$ | H | $(CH_2)_3CH_3$ | 0 |
| $(CH_2)_3CH_3$ | $4-CH_3OC_6H_4$ | $4-FC_6H_4$ | $CH_3$ | $CH_2CH=CH$ | 1 |
| $CHF_2$ | $4-FC_6H_4$ | $4-ClC_6H_4$ | H | $(CH_2)_2N(CH_3)_2$ | 2 |
| $CH_3$ | $4-FC_6H_4$ | $3,4-diClC_6H_3$ | H | $\phi CH_2OCH_2$ | 0 |
| $CF_3$ | $4-FC_6H_4$ | $4-BrC_6H_4$ | H | $CH_3OCH_2$ | 0 |
| $CF_3$ | 3-pyridyl | $4-FC_6H_4$ | H | $CH_3CH_2OCH$<br>\|<br>$CH_3$ | 0 |
| $CF_3$ | $4-FC_6H_4$ | $4-ClC_6H_4$ | $CH_3(CH_2)$ | $n-C_3H_7OCH_2$ | 2 |
| $CF_3$ | $4-ClC_6H_4$ | $4-FC_6H_4$ | H | $CH_2OCCH_2\phi$<br>\|\|<br>$O$ | |
| $CH_2CF_3$ | 2-thienyl | $4-CH_3CH_2OC_6H_4$ | H | $CH_2OCC(CH_3)_3$<br>\|\|<br>$O$ | 0 |
| $CH_2CH_3$ | $4-FC_6H_4$ | $4-FC_6H_4$ | H | 2-tetrahydro- | 0 |

TABLE VIA-continued

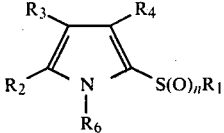

| R₁ | R₂ | R₃ | R₄ | R₆ | n |
|---|---|---|---|---|---|
| CH₂CF₃ | 3-CH₃C₆H₄ | 3-CH₃C₆H₄ | H | pyranyl 2-tetrahydrofuryl | 2 |
| (CH₂)₂CH₃ | 3-pyridyl-N-oxide | 2-FC₆H₄ | CH₃ | COCH₃ (‖O) | 1 |
| CF₃ | 4-CH₃OC₆H₄ | 4-FC₆H₄ | H | CO(CH₂)₃CH₃ (‖O) | 1 |
| CF₃ | 4-FC₆H₄ | 4-N(CH₃)₂C₆H₄ | H | COCH₂φ (‖O) | 1 |
| (CH₂)₂CH₂F | 3,4-diClC₆H₃ | 4-FC₆H₄ | H | CCH₃ (‖O) | 1 |
| CF₃ | 4-FC₆H₄ | 3-BrC₆H₄ | H | C(CH₂)₂CH₃ (‖O) | 2 |
| CF₃ | 4-FC₆H₄ | 2-ClC₆H₄ | H | C—CH₂φ (‖O) | 0 |
| CH₂CF₃ | 4-FC₆H₄ | 2-CH₃OC₆H₄ | CH₃ | C₆H₅CO | 0 |
| CF₃ | 3-pyridyl | 4-FC₆H₄ | H | 4-FC₆H₄CO | 0 |
| CH₃ | 4-FC₆H₄ | 2-FC₆H₄ | H | 3-CH₃C₆H₄CO | 0 |
| CF₃ | 4-CH₃OC₆H₄ | 4-FC₆H₄ | H | 2-CH₃OC₆H₄CO | 2 |
| CH₂CH₃ | 4-FC₆H₄ | 3-ClC₆H₄ | H | 4-NO₂C₆H₄CO | 1 |
| CH₂CF₃ | 4-FC₆H₄ | 3,4-diClC₆H₃ | H | C₆H₅SO₂ | 0 |
| CF₃ | 4-FC₆H₄ | 4-FC₆H₄ | CH₃CH₂ | 4-ClC₆H₄SO₂ | 0 |
| CH₃ | 2-thienyl | 4-F-3-CH₃OC₆H₃ | H | 2-CH₃CH₂C₆H₄SO₂ | 2 |
| CF₃ | 4-ClC₆H₄ | 4-FC₆H₄ | H | 3-CH₃(CH₂)₂OC₆H₄SO₂ | 0 |
| CF₃ | 3-pyridyl-N-oxide | 3-FC₆H₄ | H | 3-NO₂C₆H₄SO₂ | 2 |
| CF₃ | 4-FC₆H₄ | 4-BrC₆H₄ | H | CH₃SO₂ | 1 |
| CH₂CH=CH₂ | 4-FC₆H₄ | 4-CH₃OC₆H₄ | H | CH₃(CH₂)₃SO₂ | 0 |
| CH₃ | 2-BrC₆H₄ | 2-BrC₆H₄ | CH₃ | CN(CH₃)₂ (‖O) | 2 |
| CH₂F | 4-FC₆H₄ | 3-FC₆H₄ | H | n-C₄H₉SO₂— | 0 |
| CF₃ | 4-FC₆H₄ | 4-FC₆H₄ | H | CN(CH₂CH₃)₂ (‖S) | 1 |
| CF₃ | 4-FC₆H₄ | 4-F₆H₄ | H | CH₃ | 2 |
| CF₃ | 3,4-diFC₆H₃ | 4-FC₆H₄ | H | COCH₃ | 0 |
| (CH₂)₃CH₂F | 4-CH₃(CH₂)₃C₆H₄ | 4-CH₃(CH₂)₃—OC₆H₄ | H | CH₂OCH₂CH₂OCH₃ | 0 |
| CF₃ | 4-FC₆H₄ | 3-Cl-4FC₆H₃ | H | CH₂OCCH₃ (‖O) | 1 |
| CH₃ | 3-ClC₆H₄ | 4-FC₆H₄ | H | φCH₂CO | 0 |
| CF₃ | 2-BrC₆H₄ | 3-ClC₆H₄ | H | CH₃(CH₂)₃CO | 0 |
| CF₃ | 4-CH₃CH₂OC₆H₄ | 2-CH₃C₆H₄ | H | 4-Cl-C₆H₄CO | 1 |
| CH₂CH=CH₂ | 4FC₆H₄ | 4-FC₆H₄ | H | 4-FC₆H₄SO₂ | 0 |

Dosage Forms

The anti-arthritic agents and analgesic agents of this invention can be administered to treat arthritis or alleviate pain by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.05 to 40 milligrams per kilogram of body weight. Ordinarily 0.1 to 20, and preferably 0.2 to 10 milligrams per kilogram per day given in divided doses 2 to 4 times a day or in sustained release form is effective to obtain desired results.

Dosage forms (compositions) suitable for internal administration contain from about 5 milligrams to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tables. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in Remington's Pharmaceutical Sciences, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 50 milligrams of powdered active ingredient, 110 milligrams of lactose, 32 milligrams of talc, and 8 milligrams magnesium stearate.

Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

Pharmaceutical Utility

A procedure for detecting and comparing the antiinflammatory activity of compounds in this series and standard drugs for which there is a good correlation with human efficacy is the adjuvant-induced arthritis test in rats.

A procedure for detecting and comparing the analgesic activity of compounds in this series and standard drugs for which there is a good correlation with human efficacy is the phenylquinone writhing test.

The test procedures employed for determining antiinflammatory and analgesic activity are described below with test data included in Tables VII and VIII.

Established Adjuvant-Induced Arthritis in Rats

Charles River Lewis male rats (130–150 grams) are injected subcutaneously in plantar area of the right hind paw with 0.1 ml of adjuvant (Difco heat-killed, lyophilized *Mycobacterium butyricum* suspended in mineral oil 5 mg/ml). 20 Non-arthritic controls are injected with mineral oil. The animals are held for 2 weeks to allow development of arthritis. Paw volumes (uninjected, left hind paw) are measured and the adjuvant injected rats are culled and distributed to treatment groups of 10 of equal disease severity. Non-arthritic controls are distributed to 2 groups of 10. The rats are given oral doses of compound or PVA-Acacia (Polyvinyl Alcohol 1%, Gum Acacia, U.S.P. 5%, Methylparaben 0.5%) (10 ml/kg) by gavage on that day and on the 6 following days. One day after the last dose the paw volumes (uninjected, left hind paw) are measured using a Ugo Basile Volume Differential Meter Model 7101.

$$\frac{\text{Arthritic Control Mean Paw Volume (ml)} - \text{Treatment Group Mean Paw Volume (ml)}}{\text{Arthritic Control Mean Paw Volume (ml)} - \text{Non-Arthritic Control Mean Paw Volume (ml)}} \times 100 =$$

% Decrease from Control Mean Paw Volume.

Dose-response regression lines of the % decrease are plotted on semi-log paper by visual fit and the ED50% decrease from control paw volume is determined by inspection.

Phenylquinone Writhing Test

The phenylquinone writhing test, modified from Siegmund, et al., *Proc. Soc. Exp. Biol. Med.* 95, 729 (1957), was employed. A test compound suspended in 1% methylcellulose was given orally to fasted (17–21 hours) female white mice, 5–20 animals per double blind test. Aqueous (0.01% phenyl-p-benzoquinone) phenylquinone was injected intraperitoneally at 24 minutes later using 0.20 ml per mouse. Commencing at 30 minutes after the oral administration of the test compound, the mice were observed for 10 minutes for a characteristic stretching or writhing syndrome which is indicative of pain induced by phenylquinone. The effective analgesic dose for 50% of the mice ($ED_{50}$) was calculated by the moving average method of Thompson, W. R., *Bact. Rev.* 11, 115–145 (1947).

TABLE VII
Biological Activity $$\text{Ar}-\text{C}=\text{C}-\text{Ar'}... \text{N(H)}...\text{S(O)}_n\text{R}_1$$

(2,5-diaryl pyrrole with S(O)$_n$R$_1$ substituent, N-H)

| Example | Ar | Ar' | R$_1$ | n | Adjuvant Arthritis[1] ED$_{50}$ (mg/kg) | Analgesic ED$_{50}$ (mg/kg) |
|---|---|---|---|---|---|---|
| 1 | C$_6$H$_5$ | C$_6$H$_5$ | CF$_3$ | 0 | (36%/25) | >135 |
| 2 | 4-CH$_3$OC$_6$H$_4$ | 4-CH$_3$OC$_6$H$_4$ | CF$_3$ | 0 | 1.7 | 30 |
| 3 | 4-FC$_6$H$_4$ | 4-FC$_6$H$_4$ | CF$_3$ | 0 | 1.5 | >135 |
| 4 | 4-ClC$_6$H$_4$ | 4-ClC$_6$H$_4$ | CF$_3$ | 0 | 2.8 | >130 |
| 5 | 4-FC$_6$H$_4$ | 4-C$_2$H$_5$OC$_6$H$_4$ | CF$_3$ | 0 | (19%/27) | >130 |
| 6 | 4-ClC$_6$H$_4$ | 4-FC$_6$H$_4$ | CF$_3$ | 0 | 2.0 | >108 |
| 7 | 4-FC$_6$H$_4$ | 4-ClC$_6$H$_4$ | CF$_3$ | 0 | 1.1 | >108 |
| 8 | 4-FC$_6$H$_4$ | 4-CH$_3$OC$_6$H$_4$ | CF$_3$ | 0 | 30 | 26 |
| 9 | 4-ClC$_6$H$_4$ | 4-CH$_3$OC$_6$H$_4$ | CF$_3$ | 0 | 6.0 | >108 |
| 10 | 4-FC$_6$H$_4$ | C$_6$H$_5$ | CF$_3$ | 0 | (22%/27) | >108 |
| 11 | 4-ClC$_6$H$_4$ | C$_6$H$_5$ | CF$_3$ | 0 | 25 | >108 |
| 12 | 4-CH$_3$C$_6$H$_4$ | 4-CH$_3$C$_6$H$_4$ | CF$_3$ | 0 | 25 | 16.2 |
| 13 | 3-FC$_6$H$_4$ | 3-FC$_6$H$_4$ | CF$_3$ | 0 | (33%/27) | >108 |
| 16 | C$_6$H$_5$ | 3,4-diClC$_6$H$_3$ | CF$_3$ | 0 | 2.5 | >108 |
| 35 | 4-FC$_6$H$_4$ | 4-FC$_6$H$_4$ | CHF$_2$CF$_2$ | 0 | 4.0 | >108 |
| 36 | 4-CH$_3$OC$_6$H$_4$ | 4-CH$_3$OC$_6$H$_4$ | CH$_3$ | 0 | 5.0 | >130 |
| 38 | 4-ClC$_6$H$_4$ | 4-ClC$_6$H$_4$ | CH$_3$ | 0 | 10 | >108 |
| 40 | 4-ClC$_6$H$_4$ | 4-ClC$_6$H$_4$ | CHF$_2$CF$_2$ | 0 | (36%/9) | >108 |
| 41 | 4-FC$_6$H$_4$ | 4-FC$_6$H$_4$ | CH$_3$ | 0 | (19%/27) | >108 |
| 43 | 4-ClC$_6$H$_4$ | 4-FC$_6$H$_4$ | CH$_3$ | 0 | 20 | >108 |
| 44 | 4-FC$_6$H$_4$ | 4-ClC$_6$H$_4$ | CH$_3$ | 0 | 25 | >108 |
| 45 | 4-FC$_6$H$_4$ | 4-CH$_3$OC$_6$H$_4$ | CH$_3$ | 0 | 37 | 78 |
| 46 | 4-ClC$_6$H$_4$ | 4-CH$_3$OC$_6$H$_4$ | CH$_3$ | 0 | 23 | 63 |
| 47 | 4-FC$_6$H$_4$ | C$_6$H$_5$ | CH$_3$ | 0 | (46%/200) | — |
| 48 | 4-ClC$_6$H$_4$ | C$_6$H$_5$ | CH$_3$ | 0 | (22%/45) | >108 |
| 49 | 4-CH$_3$C$_6$H$_4$ | 4-CH$_3$C$_6$H$_4$ | CH$_3$ | 0 | 50 | >135 |
| 51 | C$_6$H$_5$ | C$_6$H$_5$ | CF$_3$ | 2 | (46%/25) | 15 |
| 52 | C$_6$H$_5$ | C$_6$H$_5$ | CF$_3$ | 1 | (31%/25) | 30 |
| 53 | 4-CH$_3$OC$_6$H$_4$ | 4-CH$_3$OC$_6$H$_4$ | CF$_3$ | 2 | (36%/9) | 78 |
| 54 | 4-CH$_3$OC$_6$H$_4$ | 4-CH$_3$OC$_6$H$_4$ | CH$_3$ | 2 | 1.0 | 16 |
| 55 | 4-CH$_3$OC$_6$H$_4$ | 4-CH$_3$OC$_6$H$_4$ | CH$_3$CH$_2$ | 2 | 9 | 19 |
| 56 | 4-FC$_6$H$_4$ | 4-FC$_6$H$_4$ | CF$_3$ | 2 | 1.4 | >135 |
| 57 | 4-FC$_6$H$_4$ | 4-FC$_6$H$_4$ | CF$_3$ | 1 | 1.0 | >135 |
| 58 | 4-ClC$_6$H$_4$ | 4-ClC$_6$H$_4$ | CF$_3$ | 2 | 1.7 | <130 |
| 59 | 4-ClC$_6$H$_4$ | 4-ClC$_6$H$_4$ | CF$_3$ | 1 | 2.7 | >135 |
| 60 | 4-FC$_6$H$_4$ | 4-C$_2$H$_5$OC$_6$H$_4$ | CF$_3$ | 2 | 16 | >130 |
| 61 | 4-FC$_6$H$_4$ | 4-C$_2$H$_5$OC$_6$H$_4$ | CF$_3$ | 1 | (14%/9) | >130 |
| 62 | 4-ClC$_6$H$_4$ | 4-ClC$_6$H$_4$ | CH$_3$ | 2 | 1.5 | >108 |
| 63 | 4-FC$_6$H$_4$ | 4-C$_2$H$_5$OC$_6$H$_4$ | CH$_3$ | 2 | (34%/25) | >108 |
| 64 | 4-FC$_6$H$_4$ | 4-FC$_6$H$_4$ | CH$_3$ | 2 | (25%/27) | >108 |
| 65 | 4-ClC$_6$H$_4$ | 4-ClC$_6$H$_4$ | CH$_3$CH$_2$ | 2 | (23%/27) | >108 |
| 66 | 4-ClC$_6$H$_4$ | 4-FC$_6$H$_4$ | CH$_3$ | 2 | 27 | >135 |
| 67 | 4-FC$_6$H$_4$ | 4-ClC$_6$H$_4$ | CH$_3$ | 2 | 50 | 38 |
| 68 | 4-FC$_6$H$_4$ | 4-CH$_3$OC$_6$H$_4$ | CH$_3$ | 2 | (34%/27) | 18 |
| 69 | 4-ClC$_6$H$_4$ | 4-CH$_3$OC$_6$H$_4$ | CH$_3$ | 2 | 13 | 38 |
| 71 | 4-ClC$_6$H$_4$ | C$_6$H$_5$ | CH$_3$ | 2 | (23%/27) | >108 |
| 72 | 4-CH$_3$C$_6$H$_4$ | 4-CH$_3$C$_6$H$_4$ | CH$_3$ | 2 | 90 | 7.2 |

[1]Values in parenthesis represent the percent reduction in paw volume at the indicated dose.

TABLE VIII
Biological Activity (pyrrole with Ar, Ar', R$_4$, R$_6$ on N, and S(O)$_n$R$_1$)

| Example | Ar | Ar' | R$_1$ | n | R$_4$ | R$_6$ | Adjuvant Arthritis ED$_{50}$ | Analgesic ED$_{50}$ |
|---|---|---|---|---|---|---|---|---|
| 17 | C$_6$H$_5$ | 3-pyridyl | CF$_3$ | 0 | H | H | 1.4 | >108 |
| 18 | 4-CH$_3$OC$_6$H$_4$ | 2-thienyl | CF$_3$ | 0 | H | H | ~100 | 78 |
| 74 | 4-FC$_6$H$_4$ | 4-FC$_6$H$_4$ | CF$_3$ | 0 | H | CH$_3$ | 1.1 | >108 |
| 73 | 4-FC$_6$H$_4$ | 4-FC$_6$H$_4$ | CF$_3$ | 0 | H | C(O)CH$_3$ | 4.0 | >108 |
| 76 | 4-FC$_6$H$_4$ | 4-FC$_6$H$_4$ | CF$_3$ | 0 | H | C(O)C$_6$H$_5$ | 6.6 | >108 |
| 77 | 4-FC$_6$H$_4$ | 4-FC$_6$H$_4$ | CF$_3$ | 0 | H | SO$_2$C$_6$H$_5$ | (37%/9.0) | — |
| 75 | 4-FC$_6$H$_4$ | 4-FC$_6$H$_4$ | CF$_3$ | 0 | H | COOC$_2$H$_5$ | 1.9 | >108 |
| 15 | C$_6$H$_5$ | C$_6$H$_5$ | CF$_3$ | 0 | CH$_3$ | H | 7.5 | >108 |

TABLE VIII-continued

Biological Activity

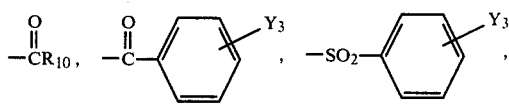

| Example | Ar | Ar' | $R_1$ | n | $R_4$ | $R_6$ | Adjuvant Arthritis $ED_{50}$ | Analgesic $ED_{50}$ |
|---|---|---|---|---|---|---|---|---|
| 19 | 2-$FC_6H_4$ | 2-$FC_6H_4$ | $CF_3$ | 0 | H | H | (29%/45) | >108 |
| 20 | $C_6H_5$ | 4-$CH_3OC_6H_4$ | $CF_3$ | 0 | H | H | (44%/27) | 22 |
| 21 | 4-$FC_6H_4$ | 4-$BrC_6H_4$ | $CF_3$ | 0 | H | H | 3.5 | >108 |
| 22 | 4-$FC_6H_4$ | 4-$(CH_3)_2NC_6H_4$ | $CF_3$ | 0 | H | H | 8.8 | >108 |
| 23 | $C_6H_5$ | 4-$FC_6H_4$ | $CF_3$ | 0 | H | H | (27%/27) | >108 |
| 24 | $C_6H_5$ | 4-$ClC_6H_4$ | $CF_3$ | 0 | H | H | 10 | >135 |
| 25 | 3-$ClC_6H_4$ | 3-$ClC_6H_4$ | $CF_3$ | 0 | H | H | 25 | >108 |
| 26 | 4-$FC_6H_4$ | 4-$CH_3SC_6H_4$ | $CF_3$ | 0 | H | H | 0.6 | >108 |
| 27 | 4-$FC_6H_4$ | 2-thienyl | $CF_3$ | 0 | H | H | ~27 | >108 |
| 28 | 4-$FC_6H_4$ | 3-pyridyl | $CF_3$ | 0 | H | H | 0.04 | >135 |
| 29 | 4-$FC_6H_4$ | 4-$CH_3SO_2C_6H_4$ | $CF_3$ | 0 | H | H | 0.15 | >108 |
| 30 | 4-$ClC_6H_4$ | 4-$ClC_6H_4$ | $CF_3$ | 0 | $CH_3$ | H | 2 | >108 |
| 31 | 4-$FC_6H_4$ | 4-$FC_6H_4$ | $CF_3$ | 0 | $CH_3$ | H | 0.6 | >135 |
| 32 | 4-$CH_3OC_6H_4$ | 4-$CH_3OC_6H_4$ | $CF_3$ | 0 | $CH_3$ | H | 2.2 | — |
| 33 | 4-$FC_6H_4$ | 4-$FC_6H_4$ | $CF_3$ | 0 | $CH_3CH_2CH_2$ | H | 6.5 | >108 |

"Consisting essentially of" is intended to have its customary meaning: namely, that all specified materials and conditions are very important in practicing the invention but that unspecified materials and conditions are not excluded so long as they do not prevent the benefits of the invention from being realized.

What is claimed is:

1. A compound of the formula

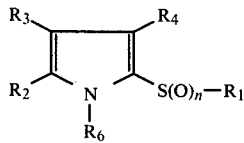

where $R_1$ = $C_1$-$C_4$ alkyl, $C_1$-$C_4$ mono- or polyfluoroalkyl or allyl;

$R_2$ and $R_3$, independently, = 2-thienyl, 3-pyridyl, 3-pyridyl-N-oxide or

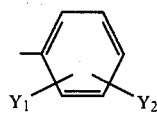

$Y_1$ = $C_1$-$C_4$ alkyl, $C_1$-$C_4$ alkoxy, F, Cl, Br, H, $(R_5)_2N$ or $R_5S(O)_m$, wherein $R_5$ = methyl or ethyl, and m = 0, 1, or 2;

$Y_2$ = H, F or Cl;

$R_4$ = H or $C_1$-$C_5$ alkyl;

$R_6$ = H, $C_1$-$C_4$ alkyl, allyl, —$CH_2CH_2N(R_7)_2$,

—CHOR$_9$,
|
R$_8$ 2-tetrahydropyranyl, 2-tetrahydrofuranyl,

—$CN(R_{11})_2$, $C_1$-$C_4$ alkylsulfonyl, or —$COR_{10}$;

$R_7$ = H, methyl or ethyl;

$R_8$ = H or methyl;

$R_9$ = $C_1$-$C_3$ alkyl, benzyl, —$CH_2CH_2OCH_3$, or $$-\overset{O}{\underset{\|}{C}}R_{10};$$

$R_{10}$ = $C_1$-$C_4$ alkyl or benzyl;

$R_{11}$ = methyl or ethyl;

X = O or S;

$Y_3$ = H, F, Cl, Br, $C_1$-$C_4$ alkyl, $C_1$-$C_4$ alkoxy or nitro; and n = 0, 1 or 2;

provided that when $R_2$ and $R_3$ both =

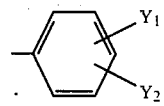

where $Y_1$ and $Y_2$ both = H, $R_1$ is $CF_3$; and further provided that when $R_1$ = $CH_3$, $R_2$ =

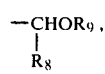

$R_3$ = 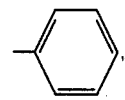

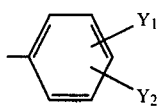

where one of $Y_1$ and $Y_2 = F$ and the other is H,
$R_4 = H$ and $R_6 = H$,
n cannot be 2;
or its pharmaceutically suitable acid addition salt where at least one of
$R_2$ or $R_3 = $ 3-pyridyl, $Y_1 = (R_5)_2N$, or
$R_6 = -CH_2CH_2N(R_7)_2$.

2. A compound of claim 1 where
$R_1 = $ methyl or trifluoromethyl.

3. A compound of claim 2 where
$R_1 = $ methyl and $n = 2$.

4. A compound of claim 2 where
$R_1 = $ trifluoromethyl and $n = 2$.

5. A compound of claim 1 where $R_2$ and $R_3$, independently are

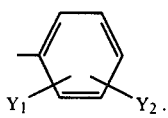

6. A compound of claim 5 where
$Y_1 = F$, Cl or methoxy.

7. A compound of claim 6 where
$Y_1 = F$.

8. A compound of claim 5 where
$Y_2 = H$.

9. A compound of claim 1 where
$R_2 = $ 3-pyridyl.

10. A compound of claim 1 where
$R_6 = H$.

11. A compound of claim 1 where
$n = 0$ or 2.

12. A compound of claim 11 where
$n = 2$.

13. A compound of claim 5 where
$R_1 = $ methyl or trifluoromethyl;
$R_4 = H$;
$R_6 = H$;
$n = 0$ or 2;
$Y_1 = F$, Cl, or methoxy; and
$Y_2 = H$.

14. A compound of claim 13 where
$Y_1 = F$.

15. A compound of claim 13 where
$n = 2$.

16. A compound of claim 1 where
$R_4 = H$.

17. A compound of claim 10 where $R_2$ and $R_3$, independently, are

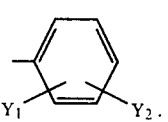

18. A compound of claim 10 where
$R_2 = $ 3-pyridyl.

19. A compound of claim 1 where
$R_1 = CF_3$;
$R_2$ and $R_3$ both =

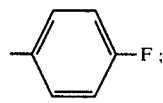

$R_4 = H$;
$R_6 = H$; and
$n = 0$, 1 or 2.

20. The compound of claim 1 where
$R_1 = CF_3$;
$R_2 = $ 3-pyridyl;
$R_3 = C_6H_5$;
$R_4 = H$;
$R_6 = H$; and
$n = 0$.

21. A pharmaceutical composition consisting essentially of a suitable pharmaceutical carrier and an effective antiinflammatory amount of a compound of claim 1.

22. A pharmaceutical composition consisting essentially of a suitable pharmaceutical carrier and an effective antiinflammatory amount of a compound of claim 2.

23. A pharmaceutical composition consisting essentially of a suitable pharmaceutical carrier and an effective antiinflammatory amount of a compound of claim 3.

24. A pharmaceutical composition consisting essentially of a suitable pharmaceutical carrier and an effective antiinflammatory amount of a compound of claim 4.

25. A pharmaceutical composition consisting essentially of a suitable pharmaceutical carrier and an effective antiinflammatory amount of a compound of claim 5.

26. A pharmaceutical composition consisting essentially of a suitable pharmaceutical carrier and an effective antiinflammatory amount of a compound of claim 6.

27. A pharmaceutical composition consisting essentially of a suitable pharmaceutical carrier and an effective antiinflammatory amount of a compound of claim 7.

28. A pharmaceutical composition consisting essentially of a suitable pharmaceutical carrier and an effective antiinflammatory amount of a compound of claim 8.

29. A pharmaceutical composition consisting essentially of a suitable pharmaceutical carrier and an effective antiinflammatory amount of a compound of claim 9.

30. A pharmaceutical composition consisting essentially of a suitable pharmaceutical carrier and an effective antiinflammatory amount of a compound of claim 10.

31. A pharmaceutical composition consisting essentially of a suitable pharmaceutical carrier and an effective antiinflammatory amount of a compound of claim 11.

32. A pharmaceutical composition consisting essentially of a suitable pharmaceutical carrier and an effective antiinflammatory amount of a compound of claim 12.

33. A pharmaceutical composition consisting essentially of a suitable pharmaceutical carrier and an effective antiinflammatory amount of a compound of claim 13.

34. A pharmaceutical composition consisting essentially of a suitable pharmaceutical carrier and an effective antiinflammatory amount of a compound of claim 14.

35. A pharmaceutical composition consisting essentially of a suitable pharmaceutical carrier and an effective antiinflammatory amount of a compound of claim 15.

36. A pharmaceutical composition consisting essentially of a suitable pharmaceutical carrier and an effective antiinflammatory amount of a compound of claim 16.

37. A pharmaceutical composition consisting essentially of a suitable pharmaceutical carrier and an effective antiinflammatory amount of a compound of claim 17.

38. A pharmaceutical composition consisting essentially of a suitable pharmaceutical carrier and an effective antiinflammatory amount of a compound of claim 18.

39. A pharmaceutical composition consisting essentially of a suitable pharmaceutical carrier and an effective antiinflammatory amount of a compound of claim 19.

40. A pharmaceutical composition consisting essentially of a suitable pharmaceutical carrier and an effective antiinflammatory amount of the compound of claim 20.

41. A method of treating arthritis in a mammal which comprises administering to the mammal an antiarthritic amount of a compound of claim 1.

42. A method of treating arthritis in a mammal which comprises administering to the mammal an antiarthritic amount of a compound of claim 2.

43. A method of treating arthritis in a mammal which comprises administering to the mammal an antiarthritic amount of a compound of claim 3.

44. A method of treating arthritis in a mammal which comprises administering to the mammal an antiarthritic amount of a compound of claim 4.

45. A method of treating arthritis in a mammal which comprises administering to the mammal an antiarthritic amount of a compound of claim 5.

46. A method of treating arthritis in a mammal which comprises administering to the mammal an antiarthritic amount of a compound of claim 6.

47. A method of treating arthritis in a mammal which comprises administering to the mammal an antiarthritic amount of a compound of claim 7.

48. A method of treating arthritis in a mammal which comprises administering to the mammal an antiarthritic amount of a compound of claim 8.

49. A method of treating arthritis in a mammal which comprises administering to the mammal an antiarthritic amount of a compound of claim 9.

50. A method of treating arthritis in a mammal which comprises administering to the mammal an antiarthritic amount of a compound of claim 10.

51. A method of treating arthritis in a mammal which comprises administering to the mammal an antiarthritic amount of a compound of claim 11.

52. A method of treating arthritis in a mammal which comprises adminstering to the mammal an antiarthritic amount of a compound of claim 12.

53. A method of treating arthritis in a mammal which comprises administering to the mammal an antiarthritic amount of a compound of claim 13.

54. A method of treating arthritis in a mammal which comprises administering to the mammal an antiarthritic amount of a compound of claim 14.

55. A method of treating arthritis in a mammal which comprises administering to the mammal an antiarthritic amount of a compound of claim 15.

56. A method of treating arthritis in a mammal which comprises administering to the mammal an antiarthritic amount of a compound of claim 16.

57. A method of treating arthritis in a mammal which comprises administering to the mammal an antiarthritic amount of a compound of claim 17.

58. A method of treating arthritis in a mammal which comprises administering to the mammal an antiarthritic amount of a compound of claim 18.

59. A method of treating arthritis in a mammal which comprises administering to the mammal an antiarthritic amount of a compound of claim 19.

60. A method of treating arthritis in a mammal which comprises administering to the mammal an antiarthritic amount of the compound of claim 20.

61. A compound of claim 1 where $R_2$ and $R_3$ independently =

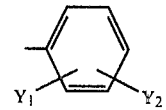

where
$Y_1 = C_1-C_4$ alkyl, $C_1-C_4$ alkoxy, F, Cl, Br, H or $(R_5)_2N$;
$Y_2 = H$, F, or Cl;
$R_4 = H$ or $C_1-C_3$ alkyl;
$R_6 = H$.

62. The compound of claim 1 where
$R_1 = CF_3$
$R_2 =$

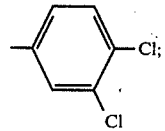

$R_3 = C_6H_5$
$R_4 = H$;
$R_6 = H$; and
$n = O$.

63. The compound of claim 1 where
$R_1 = CF_3$;
$R_2$ and $R_3$ both =

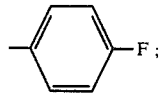

$R_4 = CH_3$;
$R_6 = H$; and
$n = O$.

64. The compound of claim 1 where $R_1 = CF_3$;

$R_2$ = 3-pyridyl;

$R_3$ = 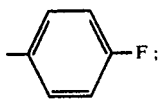

$R_4$ = H;

$R_6$ = H; and n = O.

65. A pharmaceutical composition consisting essentially of a suitable pharmaceutical carrier and an effective antiinflammatory amount of a compound of claim 61.

66. A pharmaceutical composition consisting essentially of a suitable pharmaceutical carrier and an effective antiinflammatory amount of the compound of claim 62.

67. A pharmaceutical composition consisting essentially of a suitable pharmaceutical carrier and an effective antiinflammatory amount of the compound of claim 63.

68. A pharmaceutical composition consisting essentially of a suitable pharmaceutical carrier and an effective antiinflammatory amount of the compound of claim 64.

69. A method of treating arthritis in a mammal which comprises administering to the mammal an antiarthritic amount of a compound of claim 61.

70. A method of treating arthritis in a mammal which comprises administering to the mammal an antiarthritic amount of the compound of claim 62.

71. A method of treating arthritis in a mammal which comprises administering to the mammal an antiarthritic amount of the compound of claim 63.

72. A method of treating arthritis in a mammal which comprises administering to the mammal an antiarthritic amount of the compound of claim 64.

* * * * *